United States Patent
Zur Wiesche et al.

(10) Patent No.: US 8,377,890 B2
(45) Date of Patent: Feb. 19, 2013

(54) HAIR TREATMENT AGENTS HAVING LOW-DOSE OLIGOPEPTIDES

(75) Inventors: Erik Schulze Zur Wiesche, Hamburg (DE); Petra Westphal, Neu Wulmstorf (DE); Elisabeth Poppe, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 13/039,381

(22) Filed: Mar. 3, 2011

(65) Prior Publication Data

US 2011/0274640 A1 Nov. 10, 2011

Related U.S. Application Data

(63) Continuation of application No. PCT/EP2009/060026, filed on Aug. 3, 2009.

(30) Foreign Application Priority Data

Sep. 3, 2008 (DE) .......................... 10 2008 045 511

(51) Int. Cl.
- *A61K 35/36* (2006.01)
- *A61K 38/00* (2006.01)
- *A61K 38/04* (2006.01)
- *C07K 7/00* (2006.01)
- *C07K 7/06* (2006.01)
- *C07K 7/08* (2006.01)

(52) U.S. Cl. .............. 514/20.7; 514/21.5; 514/21.6; 514/21.7; 514/21.8; 530/326; 530/327; 530/328; 530/329; 530/330

(58) Field of Classification Search .............. None
See application file for complete search history.

(56) References Cited

U.S. PATENT DOCUMENTS

| | | | |
|---|---|---|---|
| 4,865,774 A | 9/1989 | Fabry et al. | |
| 5,773,595 A | 6/1998 | Weuthen et al. | |
| 2002/0035243 A1 | 3/2002 | Imfeld et al. | |

FOREIGN PATENT DOCUMENTS

| | | |
|---|---|---|
| DE | 19540853 A1 | 5/1997 |
| DE | 102007039743 A1 | 2/2009 |
| EP | 1310511 A2 | 5/2003 |
| JP | 2002-255994 * | 9/2002 |
| WO | 9213829 A1 | 8/1992 |
| WO | 2009010314 A1 | 1/2009 |

OTHER PUBLICATIONS

Definition of derivative from http://cancerweb.ncl.ac.uk/omd/about.html, pp. 1-5. Accessed Jul. 7, 2005.*
Machine translation of JP 2002-255994, Accessed May 1, 2012.*

* cited by examiner

*Primary Examiner* — Julie Ha
(74) *Attorney, Agent, or Firm* — Ingrassia Fisher & Lorenz, P.C.

(57) ABSTRACT

A hair treatment agent having advantageous properties is provided. The hair treatment agent contains, based on weight of the agent, 0.00001 to <0.05% by weight of at least one oligopeptide having at least one amino acid sequence Glu-Glu-Glu (formula (A)),

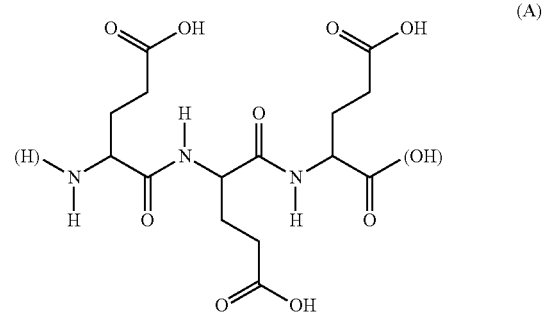

wherein the amino group may be present in a free or protonated manner, and the carboxy groups may be present in a free or deprotonated manner.

8 Claims, No Drawings

HAIR TREATMENT AGENTS HAVING LOW-DOSE OLIGOPEPTIDES

CROSS REFERENCE TO RELATED APPLICATIONS

The present application is a continuation of International Patent Application No. PCT/EP2009/060026 filed 3 Aug. 2009, which claims priority to German Patent Application No. 10 2008 045 511.3 filed 3 Sep. 2008, both of which are incorporated herein by reference.

The invention relates to hair treatment agents containing certain oligopeptides and use of these agents for the cleaning and/or care of skin and hair.

Due to the severe stressing of hair, for example, by dyeing or perms, by cleaning the hair with shampoos, and by environmental pollution, conditioning products with long-lasting effect are becoming increasingly significant. These conditioning agents affect the natural structure and properties of hair. Thus, following such treatments, for example, wet and dry combability of hair or the hold and body of hair can be optimized, or hairs can be protected from an increase in split ends.

For a long time, it has been common to subject the hair to a special after-treatment. This involves a hair treatment, usually in the form of a rinse, with special active substances, for example, quaternary ammonium salts or special polymers. As a result of this treatment, depending on the formulation, the hold and body of the hair are improved and the rate of split end formation is reduced.

Known active substances cannot meet all requirements to a sufficient extent, however. A need therefore still exists for active substances or active substance combinations for cosmetic agents having good conditioning properties and good biodegradability. In formulations containing dye and/or electrolytes in particular, there is a need for additional active conditioning substances which can be incorporated into known formulations without any problems and the action of which is not diminished there due to incompatibilities with other ingredients.

It has now been found that particularly advantageous results are achieved if certain oligopeptides are incorporated into hair treatment agents.

The present invention firstly provides hair treatment agents containing 0.00001 to <0.05 wt. % of at least one oligopeptide having at least one amino acid sequence Glu-Glu-Glu, wherein the amino group may be present in a free or protonated form and the carboxy groups may be present in a free or deprotonated form.

In this and in all following formulae, the hydrogen atom of the amino group in brackets and the hydroxyl group of the acid function in brackets signify that those groups may be present as such (in which case it is an oligopeptide with the particular number of amino acids as illustrated (in the above formula 3) or that the amino acid sequence is present in an oligopeptide having additional amino acids—depending on where the additional amino acid(s) is/are bound, the components in brackets in the aforementioned formula are replaced by the additional amino acid residue(s).

Hair treatment agents according to the present invention include hair shampoos, hair conditioners, conditioning shampoos, hairsprays, hair rinses, intensive hair conditioners, hair masques, hair tonics, perm fixing solutions, hair coloring shampoos, hair dyes, hair fixatives, hair setting compositions, hairstyling preparations, blow-drying lotions, styling mousses, hair gels, hair waxes or combinations thereof. Since men are often reluctant to use several different agents and/or several application steps, agents according to the invention are preferably those in which a man would use regardless. Preferred agents according to the invention are therefore shampoos, conditioners or hair tonics.

Hair treatment agents according to the invention contain, based on total weight of the agent, −0.00001 to ≦0.05 wt. % of at least one oligopeptide having at least one amino acid sequence Glu-Glu-Glu (i.e., at least three consecutive glutamic acids).

Oligopeptides within the meaning of the present application are condensation products of amino acids having at least 3 and a maximum of 25 amino acids linked by amide-type peptide bonds.

In preferred hair treatment agents, the oligopeptide has 5 to 15 amino acids, preferably 6 to 13 amino acids, more preferably 7 to 12 amino acids and particularly 8, 9 or 10 amino acids.

Depending on whether additional amino acids are bonded to the Glu-Glu-Glu sequence, and depending on the nature of these amino acids, the molar mass of the oligopeptide present in the agents can vary. Preferred hair treatment agents according to the invention are characterized in that the oligopeptide has a molar mass of 650 to 3000 Da, preferably 750 to 2500 Da, more preferably 850 to 2000 Da, and particularly 1000 to 1600 Da.

As can be seen from the preferred number of amino acids in the oligopeptides and the preferred molar mass range, oligopeptides that do not consist solely of the three glutamic acids but have additional amino acids bonded to this sequence are preferably used. These additional amino acids are preferably selected from certain amino acids, while certain other representatives are less preferred according to the invention.

For example, it is preferred if no methionine is present in the oligopeptides used in agents according to the invention.

It is further preferred if the oligopeptides used in the agents do not contain any cysteine and/or cystine.

It is further preferred if the oligopeptides used in the agents do not contain any aspartic acid and/or asparagine.

It is further preferred if the oligopeptides used in the agents do not contain any serine and/or threonine.

On the other hand, preferably the oligopeptides used in the agents contain tyrosine.

It is further preferred if the oligopeptides used in the agents contain leucine.

It is further preferred if the oligopeptides used in the agents contain isoleucine.

It is further preferred if the oligopeptides used in the agents contain arginine.

It is further preferred if the oligopeptides used in the agents contain valine.

Particularly preferred oligopeptides or amino acid sequences present in preferred oligopeptides are described below.

One particularly preferred oligopeptide additionally contains tyrosine, which is preferably bonded via its acid function to the Glu-Glu-Glu sequence. Preferred hair treatment agents are therefore characterized in that the oligopeptide present therein has at least one amino acid sequence Tyr-Glu-Glu-Glu, wherein the amino group may be present in a free or protonated form and the carboxy groups may be present in a free or deprotonated form.

Another particularly preferred oligopeptide additionally contains isoleucine, which is preferably bonded via its amino function to the Glu-Glu-Glu sequence. Preferred hair treatment agents are therefore characterized in that the oligopeptide present therein has at least one amino acid sequence Glu-Glu-Glu-Ile, wherein the amino group may be present in a free or protonated form and the carboxy groups may be present in a free or deprotonated form.

Oligopeptides having both the above amino acids (tyrosine and isoleucine) are preferred according to the invention. Particularly preferred in this case are hair treatment agents in which the oligopeptide present therein has at least one amino acid sequence Tyr-Glu-Glu-Glu-Ile, wherein the amino group may be present in a free or protonated form and the carboxy groups may be present in a free or deprotonated form.

Oligopeptides that are further preferred additionally contain arginine, preferably present bound to isoleucine.

Preferred hair treatment agents containing at least one oligopeptide having at least one amino acid sequence Glu-Glu-Glu

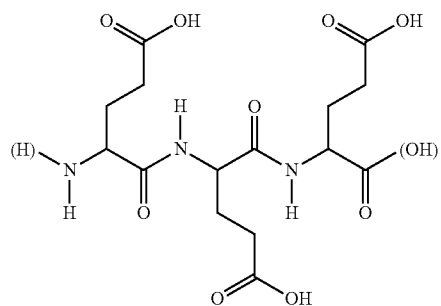

or hair treatment agents containing at least one oligopeptide having at least one amino acid sequence Tyr-Glu-Glu-Glu

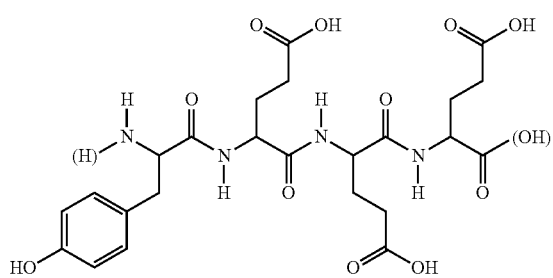

or hair treatment agents containing at least one oligopeptide having at least one amino acid sequence Glu-Glu-Glu-Ile

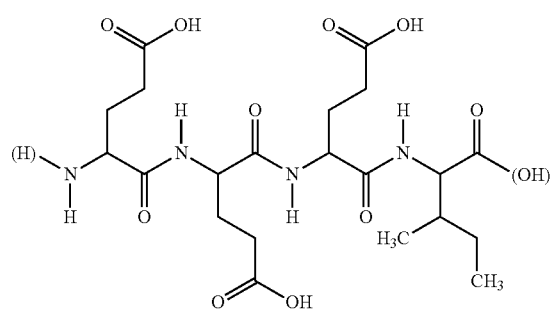

or hair treatment agents containing at least one oligopeptide having at least one amino acid sequence Tyr-Glu-Glu-Glu-Ile

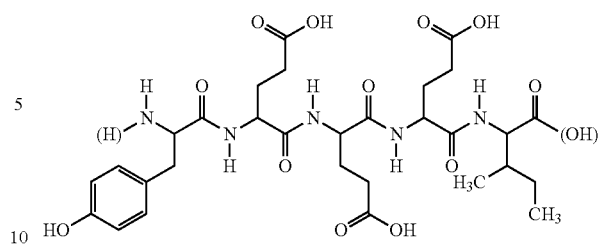

in each case wherein the amino group may be present in a free or protonated form and the carboxy groups may be present in a free or deprotonated form, wherein the oligopeptide has 5 to 15 amino acids, preferably 6 to 13 amino acids, more preferably 7 to 12 amino acids and particularly 8, 9 or 10 amino acids, wherein the oligopeptide has a molar mass of 650 to 3000 Da, preferably 750 to 2500 Da, more preferably 850 to 2000 Da and particularly 1000 to 1600 Da, further includes those wherein the oligopeptide contained therein has at least one amino acid sequence Tyr-Glu-Glu-Glu-Ile-Arg, wherein the amino groups may be present in a free or protonated form and the carboxy groups may be present in a free or deprotonated form.

Still further preferred oligopeptides additionally contain valine, preferably bound to the arginine. Further preferred hair treatment agents are those wherein the oligopeptide contained therein has at least one amino acid sequence Tyr-Glu-Glu-Glu-Ile-Arg-Val, wherein the amino groups may be present in a free or protonated form and the carboxy groups may be present in a free or deprotonated form.

Still further preferred oligopeptides additionally contain leucine, preferably bound to the valine. Further preferred hair treatment agents are those wherein the oligopeptide contained therein has at least one amino acid sequence Tyr-Glu-Glu-Glu-Ile-Arg-Val-Leu, wherein the amino groups may be present in a free or protonated form and the carboxy groups may be present in a free or deprotonated form.

Particularly preferred oligopeptides additionally contain leucine, preferably present bound to the tyrosine. Further preferred hair treatment agents are those wherein the oligopeptide contained therein has at least one amino acid sequence Leu-Tyr-Glu-Glu-Glu-Ile-Arg-Val-Leu, wherein the amino groups may be present in a free or protonated form and the carboxy groups may be present in a free or deprotonated form.

Most particularly preferred agents contain at least two oligopeptides according to the aforementioned criteria but which differ from one another. Thus, for example, hair treatment agents containing at least two different oligopeptides A and B, both containing the amino acid sequence Glu-Glu-Glu, are preferred.

These different oligopeptides A and B correspond to one another in that they carry three successive Glu amino acids in their amino acid sequence but have differences in the amino acids bound before or after the successive Glu amino acids. Different peptides with a partial correspondence are preferred, which can be greater than in the three amino acids mentioned above.

Thus, further preferred hair treatment agents contain at least two oligopeptides A and B which differ from one another and which both contain the amino acid sequence Glu-Glu-Glu-Ile.

Also preferred are hair treatment agents which contain at least two different oligopeptides A and B, wherein both contain the amino acid sequence Tyr-Glu-Glu-Glu.

Still further preferred hair treatment agents contain at least two different oligopeptides A and B, wherein both contain the amino acid sequence Glu-Glu-Glu-Ile-Arg.

Likewise still further preferred hair treatment agents contain at least two different oligopeptides A and B, wherein both contain the amino acid sequence Tyr-Glu-Glu-Glu-Ile.

Most particularly preferred hair treatment agents contain at least two different oligopeptides A and B, wherein both contain the amino acid sequence Glu-Glu-Glu-Ile-Arg.

Likewise most particularly preferred hair treatment agents contain at least two different oligopeptides A and B, wherein both contain the amino acid sequence Tyr-Glu-Glu-Glu-Ile-Arg.

Preferably, there is an even greater structural correspondence in the oligopeptides. Thus, hair treatment agents that contain at least two different oligopeptides A and B, wherein both contain the amino acid sequence Glu-Glu-Glu-Ile-Arg-Val are other preferred embodiments of the present invention.

Preferred embodiments are likewise hair treatment agents that contain at least two different oligopeptides A and B, wherein both contain the amino acid sequence Tyr-Glu-Glu-Glu-Ile-Arg-Val.

Still further preferred hair treatment agents according to the invention contain at least two different oligopeptides A and B, wherein both contain the amino acid sequence Glu-Glu-Glu-Ile-Arg-Val-Leu.

Likewise still further preferred hair treatment agents contain at least two different oligopeptides A and B, wherein both contain the amino acid sequence Tyr-Glu-Glu-Glu-Ile-Arg-Val-Leu.

Particularly preferred hair treatment agents contain at least two different oligopeptides A and B, wherein oligopeptide A has the amino acid sequence Leu-Tyr-Glu-Glu-Glu-Ile-Arg-Val-Leu, with the amino groups present in a free or protonated form and the carboxy groups present in a free or deprotonated form, and oligopeptide B has the amino acid sequence Tyr-Glu-Glu-Glu-Ile-Arg-Val-Leu, with the amino groups present in a free or protonated form and the carboxy groups present in a free or deprotonated form.

Most particularly preferred agents of this last-mentioned embodiment contain 0.00001 to 1 wt. % oligopeptide A and 0.00001 to 1 wt. % oligopeptide B, based on total weight of the agent. Further preferred agents of this last-mentioned embodiment contain 0.00005 to 0.1 wt. % oligopeptide A and 0.00005 to 0.1 wt. % oligopeptide B, based on total weight of the agent. Still further preferred agents of this last-mentioned embodiment contain 0.0001 to 0.01 wt. % oligopeptide A and 0.0001 to 0.001 wt. % oligopeptide B, based on total weight of the agent.

Use of the aforementioned oligopeptides imparts outstanding properties to hair treatment agents according to the invention. These agents impart more resilience to hairs treated therewith, which is apparent in the higher tensile strengths of the keratin fibers and in a reduction in the loss of elasticity (e.g., when damaged by atmospheric influences). In particular, the particularly preferred oligopeptides additionally stabilize the moisture balance of keratinous fibers so that combability is improved and the ageing process delayed.

Another advantage of the compositions according to the invention is that the shapeability and restructurability of keratinous fibers treated therewith is improved.

Oligopeptides used within the framework of the present invention which meet the conditions mentioned above may advantageously be obtained from keratinous materials. Preferably, these oligopeptides are used in high proportions relative to total keratinous peptide content of the agents.

Most preferably, as high a proportion as possible of all the keratinous peptides contained in the agent meet the conditions mentioned above.

Preferred hair treatment agents according to the invention are those wherein at least 0.1 wt. %, preferably at least 0.5 wt. %, more preferably at least 1 wt. %, even more preferably at least 2.5 wt. %, still more preferably at least 5 wt. % and particularly at least 10 wt. % of all the keratinous peptides present in the agent have the amino acid sequence Glu-Glu-Glu.

Further preferred hair treatment agents according to the invention are those wherein at least 0.1 wt. %, preferably at least 0.5 wt. %, particularly preferably at least 1 wt. %, more preferably at least 2.5 wt. %, still more preferably at least 5 wt. % and in particular at least 10 wt. % of all keratinous peptides contained in the agent have the amino acid sequence Glu-Glu-Glu-Ile.

Still further preferred hair treatment agents according to the invention are those wherein at least 0.1 wt. %, preferably at least 0.5 wt. %, particularly preferably at least 1 wt. %, more preferably at least 2.5 wt. %, still more preferably at least 5 wt. % and in particular at least 10 wt. % of all the keratinous peptides contained in the agent have the amino acid sequence Tyr-Glu-Glu-Glu.

Particularly preferred hair treatment agents according to the invention are those wherein at least 0.1 wt. %, preferably at least 0.5 wt. %, particularly preferably at least 1 wt. %, more preferably at least 2.5 wt. %, still more preferably at least 5 wt. % and in particular at least 10 wt. % of all the keratinous peptides contained in the agent have the amino acid sequence Tyr-Glu-Glu-Glu-Ile.

Most particularly preferred hair treatment agents according to the invention are those wherein at least 0.1 wt. %, preferably at least 0.5 wt. %, particularly preferably at least 1 wt. %, more preferably at least 2.5 wt. %, still more preferably at least 5 wt. % and in particular at least 10 wt. % of all the keratinous peptides contained in the agent have the amino acid sequence Tyr-Glu-Glu-Glu-Ile-Arg.

Still further preferred hair treatment agents according to the invention are those wherein at least 0.1 wt. %, preferably at least 0.5 wt. %, particularly preferably at least 1 wt. %, more preferably at least 2.5 wt. %, still more preferably at least 5 wt. % and in particular at least 10 wt. % of all the keratinous peptides contained in the agent have the amino acid sequence Tyr-Glu-Glu-Glu-Ile-Arg-Val.

Particularly preferred hair treatment agents according to the invention are those wherein at least 0.1 wt. %, preferably at least 0.5 wt. %, particularly preferably at least 1 wt. %, more preferably at least 2.5 wt. %, still more preferably at least 5 wt. % and in particular at least 10 wt. % of all the keratinous peptides contained in the agent have the amino acid sequence Tyr-Glu-Glu-Glu-Ile-Arg-Val-Leu.

The conditions mentioned above relate to total content in the agents of peptides originating from keratinous materials. In addition to oligopeptides of keratinous origin, it is possible to use other peptides and/or protein hydrolyzates such as those from other natural sources. For example, the additional use of wheat protein hydrolyzates is preferred (see below).

Agents according to the invention may contain other active substances and auxiliary substances. These are described below.

The agents preferably also contain at least one emulsifier or surfactant, wherein surface-active substances are referred to as surfactants or as emulsifiers according to the area of application and are chosen from anionic, cationic, zwitterionic, ampholytic and nonionic surfactants and emulsifiers.

Preferred hair treatment agents according to the invention contain 0.5 to 70 wt. %, preferably 1 to 60 wt. % and in particular 5 to 25 wt. %, based on total weight of the agent, anionic and/or nonionic and/or cationic and/or amphoteric surfactant(s).

Most particularly preferred are agents which also contain fatty alcohol(s) and/or fatty alcohol alkoxylate(s), preferably $C_{12-22}$ fatty alcohol(s) and/or $C_{12-22}$ fatty alcohol ethoxylate(s) with 10 to 30 EO units, more preferably $C_{16-18}$ fatty alcohol(s) and/or $C_{16-18}$ fatty alcohol ethoxylate(s) with 12 to 20 EO units, preferably in amounts of 5 to 20 wt. %, more preferably 7.5 to 17.5 wt. % and particularly 10 to 15 wt. %, based on total weight of the agent. In summary, preferred hair treatment agents contain 0.1 to 20 wt. %, preferably 0.25 to 17.5 wt. % and particularly 5 to 15 wt. %, based on total weight of the agent, anionic surfactant(s), particularly preferably fatty alcohol ether sulfates of the formula

wherein n is a value from 5 to 21, preferably 7 to 19, more preferably 9 to 17 and particularly 11 to 13, and k is a value of 1, 2, 3, 4, 5, 6, 7, 8, 9 or 10, preferably 1, 2 or 3 and particularly 2, and M is a cation from the group $Na^+$, $K^+NH_4^+$, ½ $Mg^{2+}$, ½ $Zn^{2+}$, preferably $Na^+$.

Preferred hair treatment agents further additionally contain amphoteric surfactant(s), preferably from the N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, each having about 8 to 24 C atoms in the alkyl group, alkylaminoacetic acids each having about 8 to 24 C atoms in the alkyl group, N-cocoalkyl aminopropionate, cocoacyl aminoethyl aminopropionate, $C_{12}$-$C_{18}$ acyl sarcosine, N-alkyl-N,N-dimethylammonium glycinates, for example, cocoalkyl dimethylammonium glycinate, N-acyl-aminopropyl-N,N-dimethylammonium glycinates, for example, cocoacyl aminopropyl dimethylammonium glycinate, 2-alkyl-3-carboxymethyl-3-hydroxyethyl imidazolines each having about 8 to 18 C atoms in the alkyl or acyl group, cocoacyl aminoethyl hydroxyethyl carboxymethyl glycinate, compounds known under the INCI name cocamidopropyl betaine, compounds known under the INCI name disodium cocoamphodiacetate, with preferred agents containing amphoteric surfactant(s) in amounts of 1 to 15 wt. %, preferably 2.5 to 12 wt. % and particularly 5 to 10 wt. %, based on total weight of the agent.

As an additional optional component, agents according to the invention may contain 0.01 to 10 wt. % of at least one polymer from the group of cationic and/or amphoteric polymers. The polymer or polymers is/are preferably used within relatively narrow quantity ranges. Thus, preferred agents according to the invention contain 0.05 to 7.5 wt. %, preferably 0.1 to 5 wt. %, more preferably 0.2 to 3.5 wt. % and in particular 0.25 to 2.5 wt. %, based on total weight of the agent, amphoteric polymer(s). Regardless of whether or not amphoteric polymers are present in the agents, further preferred agents according to the invention contain 0.05 to 7.5 wt. %, preferably 0.1 to 5 wt. %, particularly preferably 0.2 to 3.5 wt. % and in particular 0.25 to 2.5 wt. %, based on total weight of the agent, cationic polymer(s).

Preferred cationic polymers are described in the priority document on pages 21 to 25.

In summary, preferred hair treatment agents contain 0.05 to 7.5 wt. %, preferably 0.1 to 5 wt. %, more preferably 0.2 to 3.5 wt. % and particularly 0.25 to 2.5 wt. %, based on total weight of the agent, cationic polymer(s). Preferred cationic polymer(s) are chosen from poly(methacryloyl oxyethyl trimethylammonium chloride) (INCI: polyquaternium-37), quaternized cellulose derivatives (INCI: polyquaternium 10), cationic alkyl polyglycosides, cationized honey, cationic guar derivatives, polymeric dimethyl diallyl ammonium salts and copolymers thereof with esters and amides of acrylic acid and methacrylic acid, copolymers of vinylpyrrolidone with quaternized derivatives of dialkylaminoalkyl acrylate and methacrylate, vinylpyrrolidone-vinylimidazolium methochloride copolymers, quaternized polyvinyl alcohol, polyquaternium 2, polyquaternium 7, polyquaternium 17, polyquaternium 18, polyquaternium 24, and/or polyquaternium 27.

In addition to or instead of the cationic polymers, the agents according to the invention may contain amphoteric polymers. Within the framework of the present invention, amphoteric polymers that can preferably be used are described in the priority document on pages 25 to 30.

Another preferred group of ingredients which can be present in the agents are vitamins, provitamins or vitamin precursors. Preferred hair treatment agents additionally contain as conditioner 0.1 to 5 wt. %, preferably 0.2 to 4 wt. %, more preferably 0.25 to 3.5 wt. %, even more preferably 0.5 to 3 wt. %, and particularly 0.5 to 2.5 wt. %, based on total weight of the agent, vitamins and/or provitamins and/or vitamin precursors, which preferably belong to the groups A, B, C, E, F and H. Preferred agents contain panthenol ((±)-2,4-dihydroxy-N-(3-hydroxypropyl)-3,3-dimethylbutyramide, provitamin $B_5$), pantothenic acid (vitamin $B_3$, vitamin $B_5$), niacin, niacinamide or nicotinamide (vitamin $B_3$), L-ascorbic acid (vitamin C), thiamin (vitamin $B_1$), riboflavin (vitamin $B_2$, vitamin G), biotin (vitamin $B_7$, vitamin H), folic acid (vitamin $B_9$, vitamin $B_c$ or vitamin M), vitamin $B_6$, and/or vitamin $B_{12}$.

Use of certain quinones reinforces an anti-dandruff and anti-hair loss action as well as improves combability and shine. As an additional agent, agents according to the invention may therefore contain 0.0001 to 5 wt. %, based on total weight of the agent, of at least one bioquinone of formula (I)

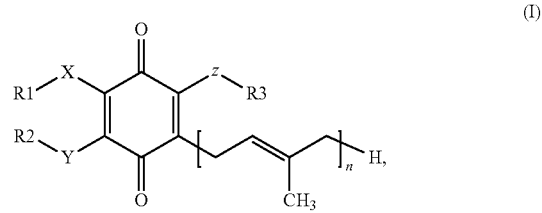

wherein

X, Y, Z are, independently of one another, —O— or —NH— or $NR^4$— or a chemical bond;

$R^1$, $R^2$, $R^3$ are, independently of one another, a hydrogen atom or an optionally substituted aryl group or an optionally substituted ($C_1$-$C_6$) alkyl group or a hydroxyalkyl group or a polyhydroxyalkyl group or an optionally substituted ($C_1$-$C_6$) alkylene group, or a ($C_1$-$C_6$) acyl residue, with preferred residues chosen from, independently of one another, —H, —$CH_3$, —$CH_2CH_3$, —$(CH_2)_2CH_2$, $CH(CH_3)_2$, —$(CH_2)_3CH_3$, —$CH(CH_3)CH_2CH_3$, —$CH_2CH(CH_3)_2$, or —$C(CH_3)_3$;

$R^4$ is —$CH_3$, —$CH_2CH_3$, —$(CH_2)_2CH_2$, —$CH(CH_3)_2$, —$(CH_2)_3CH_3$, —$CH(CH_3)CH_2CH_3$, —$CH_2CH(CH_3)_2$, or —$C(CH_3)_3$; and n is a value from 1 to 20, preferably from 2 to 15 and in particular 5, 6, 7, 8, 9, 10.

Particularly preferred hair treatment agents contain as conditioner 0.0001 to 1 wt. %, preferably 0.001 to 0.5 wt. %, and particularly 0.005 to 0.1 wt. %, based on total weight of the agent, of at least one ubiquinone and/or at least one ubiquinol and/or at least one derivative of these substances, with preferred agents containing an ubiquinone of formula (Ubi)

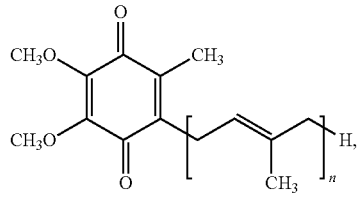
(Ubi)

wherein n is the value 6, 7, 8, 9 or 10, preferably 10 (coenzyme Q10).

As an alternative to the ubiquinones or in addition to them, the agents may also contain plastoquinones. In this case, preferred agents contain 0.0002 to 4 wt. %, preferably 0.0005 to 3 wt. %, more preferably 0.001 to 2 wt. %, even more preferably 0.0015 to 1, and particularly 0.002 to 0.5 wt. %, based on total weight of the agent, of at least one plastoquinone of formula (Ib)

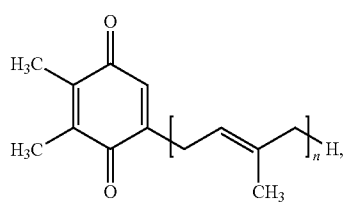
(Ib)

wherein n is a value from 1 to 20, preferably 2 to 15 and particularly 5, 6, 7, 8, 9, 10, with particularly preferred agents containing plastoquinone PQ-9 (n=9).

In order to improve the elasticity and strengthen the internal structure of hair treated with agents according to the invention, the agents may contain purine and/or purine derivatives. In particular, agents containing combinations of purine and/or purine derivatives with ubiquinones and/or plastoquinones results in hair that exhibits, inter alia, higher measurements during differential thermal analysis and improved wet and dry combability.

As an additional ingredient, the agents may therefore contain purine and/or derivative(s) of purine. Preferred agents contain purine and/or purine derivatives in relatively narrow quantity ranges. In this case, preferred cosmetic agents contain 0.001 to 2.5 wt. %, preferably 0.0025 to 1 wt. %, more preferably 0.005 to 0.5 wt. %, and particularly 0.01 to 0.1 wt. %, based on total weight of the agent, purine(s) and/or purine derivative(s).

Among purine, the purines and the purine derivatives, a few examples are particularly preferred according to the invention. Preferred hair treatment agents contain as conditioner 0.001 to 2.5 wt. %, preferably 0.0025 to 1 wt. %, more preferably 0.005 to 0.5 wt. % and particularly 0.01 to 0.1 wt. %, based on total weight of the agent, purine(s) and/or purine derivative(s), with preferred agents containing purine and/or purine derivative(s) of the formula (Pur-I)

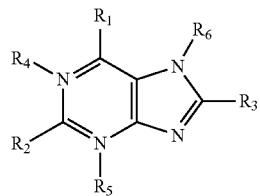
(Pur-I)

wherein $R^1$, $R^2$ and $R^3$ are, independently of one another, chosen from —H, —OH, $NH_2$, and —SH; and $R^4$, $R^5$ and $R^6$, independently of one another, are chosen from —H, —$CH_3$ and —$CH_2$—$CH_3$. The following compounds are preferred: purine ($R^1$=$R^2$=$R^3$=$R^4$=$R^5$=$R^6$=H), adenine ($R^1$=$NH_2$, $R^2$=$R^3$=$R^4$=$R^5$=$R^6$=H), guanine ($R^1$=OH, $R^2$=$NH_2$, $R^3$=$R^4$=$R^5$=$R^6$=H), ureic acid ($R^1$=$R^2$=$R^3$=OH, $R^4$=$R^5$=$R^6$=H), hypoxanthine ($R^1$=OH, $R^2$=$R^3$=$R^4$=$R^5$=$R^6$=H), purine-6-thiol ($R^1$=SH, $R^2$=$R^3$=$R^4$=$R^5$=$R^6$=H), 6-thioguanine ($R^1$=SH, $R^2$=$NH_2$, $R^3$=$R^4$=$R^5$=$R^6$=H), xanthine ($R^1$=$R^2$=OH, $R^3$=$R^4$=$R^5$=$R^6$=H), caffeine ($R^1$=$R^2$=OH, $R^3$=H, $R^4$=$R^5$=$R^6$=$CH_3$), theobromine ($R^1$=$R^2$=OH, $R^3$=$R^4$=H, $R^5$=$R^6$=$CH_3$), and theophylline ($R^1$=$R^2$=OH, $R^3$=H, $R^4$=$CH_3$, $R^5$=$CH_3$, $R^6$=H).

Depending on the desired application, the type and quantity of purine derivative may vary. In hair cosmetic formulations, caffeine has proved particularly useful and can be used, for example, in shampoos, preferably in quantities of 0.005 to 0.25 wt. %, more preferably 0.01 to 0.1 wt. %, and particularly 0.01 to 0.05 wt. %, based on total weight of the shampoo.

It is also advantageous to use purine or purine derivatives and bioquinones in a particular ratio to one another. Here, preferred agents are those in which the weight ratio of the ingredients a) and b) is 10:1 to 1:100, preferably 5:1 to 1:50, more preferably 2:1 to 1:20 and particularly 1:1 to 1:10.

As already mentioned, caffeine is a particularly preferred purine derivative, and coenzyme Q10 is a particularly preferred bioquinone. Particularly preferred agents according to the invention therefore contain 0.001 to 2.5 wt. %, preferably 0.0025 to 1 wt. %, more preferably 0.005 to 0.5 wt. %, and particularly 0.01 to 0.1 wt. % caffeine, and 0.0002 to 4 wt. %, preferably 0.0005 to 3 wt. %, more preferably 0.001 to 2 wt. %, even more preferably 0.0015 to 1, and particularly 0.002 to 0.5 wt. % coenzyme Q10, each based on total weight of the agent.

Agents according to the invention can further contain at least one carbohydrate from the group of monosaccharides, disaccharides and/or oligosaccharides. Here, preferred hair treatment agents contain as conditioner 0.01 to 5 wt. %, preferably 0.05 to 4.5 wt. %, more preferably 0.1 to 4 wt. %, even more preferably 0.5 to 3.5 wt. % and particularly 0.75 to 2.5 wt. %, bases on total weight of the agent, carbohydrate(s) chosen from monosaccharides, disaccharides and/or oligosaccharides. Preferred carbohydrates are chosen from monosaccharides (particularly D-ribose, D-xylose, L-arabinose, D-glucose, D-mannose, D-galactose, D-fructose, sorbose, L-fucose, and/or L-rhamnose) and/or disaccharides (particularly sucrose, maltose, lactose, trehalose, cellobiose, gentiobiose, and/or isomaltose).

Particularly preferred agents according to the invention contain, relative to their weight, 0.005 to 0.015 wt. % caffeine and 0.75 to 1.5 wt. % glucose monohydrate, 0.005 to 0.015 wt. % caffeine and 0.75 to 1.5 wt. % sucrose, 0.005 to 0.015 wt. % caffeine and 0.75 to 1.5 wt. % fructose.

As already mentioned, preferred agents according to the invention contain (an) amino acid(s).

Amino acids that may particularly preferably be used according to the invention originate from the group glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-cyss), L-carnitine, L-citrulline, L-theanine, 3',4'-dihydroxy-L-phenylalanine (L-dopa), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, it being possible to use both the individual amino acids and mixtures.

Preferred agents contain one or more amino acids in relatively narrow quantity ranges. Here, preferred cosmetic agents additionally contain 0.05 to 5 wt. %, preferably 0.1 to 2.5 wt. %, more preferably 0.15 to 1 wt. %, and particularly 0.2 to 0.5 wt. % amino acid(s), based on total weight of the agent. Preferably, (an) amino acid(s) from the group glycine, alanaine, valine, lysine, leucine and/or threonine is chosen.

Preferred agents according to the invention contain as conditioner 0.01 to 15 wt. %, preferably 0.025 to 12.5 wt. %, more preferably 0.05 to 10 wt. %, even more preferably 0.1 to 7.5 wt. % and particularly 0.5 to 5 wt. %, based on total weight of the agent, of at least one 2-furanone derivative of formula (Fur-I) and/or formula (Fur-Il)

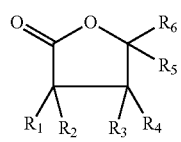

(Fur-I)

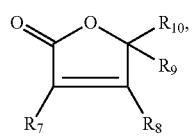

(Fur-II)

wherein $R^1$ to $R^{10}$ are, independently of one another:
hydrogen, —OH, methyl, methoxy, aminomethyl or hydroxymethyl residue,
$C_2$-$C_4$ saturated or mono- or diunsaturated, branched or linear hydrocarbon residue,
$C_2$-$C_4$ saturated or mono- or diunsaturated, branched or linear mono-, di- or trihydroxy hydrocarbon residue,
$C_2$-$C_4$ saturated or mono- or diunsaturated, branched or linear mono-, di- or triamino hydrocarbon residue,
—$OR^{11}$, with $R^{11}$ as a $C_2$-$C_4$ saturated or mono- or diunsaturated, branched or linear hydrocarbon residue,
$C_2$-$C_4$ saturated or mono- or diunsaturated, branched or linear mono-, di- or trihydroxy hydrocarbon residue,
—$NR^{12}R^{13}$, wherein $R^{12}$ and $R^{13}$ are, independently of one another in each case, hydrogen, methyl, a $C_2$-$C_4$ saturated or mono- or diunsaturated, branched or linear hydrocarbon residue, a $C_2$-$C_4$ saturated or mono- or diunsaturated, branched or linear mono-, di- or trihydroxy hydrocarbon residue,
—$COOR^{14}$, wherein $R^{14}$ is hydrogen, methyl, a $C_2$-$C_4$ saturated or mono- or diunsaturated, branched or linear hydrocarbon residue, a $C_2$-$C_4$ saturated or mono- or diunsaturated, branched or linear mono-, di- or trihydroxy hydrocarbon residue, a $C_2$-$C_4$ saturated or mono- or diunsaturated, branched or linear mono-, di- or triamino hydrocarbon residue,
—$CONR^{15}R^{16}$, wherein $R^{15}$ and $R^{16}$ are each hydrogen, methyl, a $C_2$-$C_4$ saturated or mono- or diunsaturated, branched or linear hydrocarbon residue, a $C_2$-$C_4$ saturated or mono- or diunsaturated, branched or linear mono-, di- or trihydroxy hydrocarbon residue, a $C_2$-$C_4$ saturated or mono- or diunsaturated, branched or linear mono-, di- or triamino hydrocarbon residue,
—$COR^{16}$, wherein $R^{16}$ is methyl, a $C_2$-$C_4$ saturated or mono- or diunsaturated, branched or linear hydrocarbon residue, a $C_2$-$C^4$ saturated or mono- or diunsaturated, branched or linear mono-, di- or trihydroxy hydrocarbon residue, a $C_2$-$C_4$ saturated or mono- or diunsaturated, branched or linear mono-, di- or triamino hydrocarbon residue,
a group —$OCOR^{17}$, wherein $R^{17}$ is methyl, a $C_2$-$C_{30}$ saturated or mono- or polyunsaturated, branched or linear hydrocarbon residue, a $C_2$-$C_{30}$ saturated or mono- or polyunsaturated, branched or linear mono-, di-, tri- or polyhydroxy hydrocarbon residue, a $C_2$-$C_{30}$ saturated or mono- or polyunsaturated, branched or linear mono-, di-, tri- or polyamino hydrocarbon residue,
with the proviso that, where $R^7$ and $R^8$ are —OH and at the same time $R^9$ or $R^{10}$ is hydrogen, the remaining group $R^9$ or $R^{10}$ is not a dihydroxyethyl residue.

In a most particularly preferred embodiment, dihydro-3-hydroxy-4,4-dimethyl-2(3H)-furanone is used as a compound corresponding to formula (Fur-I).

Another conditioner that can be used which possesses activating properties is taurine. Preferred hair treatment agents according to the invention contain as conditioner 0.01 to 15 wt. %, preferably 0.025 to 12.5 wt. %, more preferably 0.05 to 10 wt. %, even more preferably 0.1 to 7.5 wt. % and particularly 0.5 to 5 wt. %, based on total weight of the agent, taurine (2-aminoethanesulfonic acid).

The additional use of bisabolol and/or bisabolol oxides in agents according to the invention is also preferred. Here, hair treatment agents which also contain 0.001 to 5 wt. %, preferably 0.01 to 4 wt. %, more preferably 0.02 to 2.5 wt. % and particularly 0.1 to 1.5 wt. % bisabolol and/or oxides of bisabolol, preferably (−)-alpha-bisabolol, are preferred.

Agents according to the invention may contain, in addition to the oligopeptide(s) and other optional ingredients, other substances which prevent, alleviate or cure hair loss. In particular, a content of active substances that stabilize the hair root is advantageous. In summary, cosmetic agents containing—relative to the weight—0.001 to 5 wt. % hair root stabilizing substances, particularly Minoxidil, finasteride, and/or ketoconazole, are preferred.

With additional active anti-dandruff substances (e.g., climbazole, piroctone olamine or zinc pyrithione), the amount of the yeast fungus causing dandruff is reduced in a targeted manner, the microbial flora again reaches the normal percentage composition and flaking is reduced to the physiological level. However, laboratory tests have shown that different representatives of the species *Pityrosporum ovale* show different degrees of reaction to the active anti-dandruff substances. Therefore, in order to control all causes of dandruff to the maximum extent, a combination of active anti-dandruff substances is the most successful.

In summary, hair treatment agents additionally containing—relative to their weight—0.001 to 5 wt. % active anti-dandruff substances, particularly piroctone olamine (1-hydroxy-4-methyl-6-(2,4,4-trimethylpentyl)pyridin-2(1H)- one, compound with 2-aminoethanol, 1:1), zinc pyrithione, selenium sulfide, climbazole, and/or salicylic acid or fumaric acid, are preferred.

Agents according to the invention may additionally contain all active substances, additives and auxiliary substances known for such preparations.

It has also been shown to be advantageous if, in addition to cationic and/or amphoteric polymers, other polymers (G) are present in the agents. In a preferred embodiment, other polymers are added to the agents. Both anionic and nonionic polymers having proved effective.

Particularly preferred is the homopolymer of 2-acrylamido-2-methylpropanesulfonic acid, commercially available, for example, with the name Rheothik® 11-80.

Another polymer is present in the commercial product Sepigel®305 from SEPPIC. Use of this compound, which contains a hydrocarbon mixture ($C_{13}$-$C_{14}$ isoparaffin) and a nonionogenic emulsifier (laureth-7) in addition to the polymer component, has proved particularly advantageous.

Sodium acryloyl dimethyl taurate copolymers marketed with the name Simulgel®600 as a compound with isohexadecane and polysorbate-80 have also proved particularly effective according to the invention.

Other preferred anionic homopolymers are uncrosslinked and crosslinked polyacrylic acids. In this case, allyl ethers of pentaerythritol, of sucrose and of propylene may be preferred crosslinking agents. These compounds are commercially available, for example, with the trade name Carbopol®.

Copolymers of maleic anhydride and methyl vinyl ether, particularly those with crosslinks, are also color-retaining polymers. A maleic acid-methyl vinyl ether copolymer crosslinked with 1,9-decadiene is commercially available with the name Stabileze® QM.

In another embodiment, the agents may contain nonionogenic polymers (G4). Suitable nonionogenic polymers include:
vinylpyrrolidone/vinyl ester copolymers,
cellulose ethers such as hydroxypropyl cellulose, hydroxyethyl cellulose
starch and derivatives thereof, particularly starch ethers,
shellac,
polyvinylpyrrolidone,
siloxanes, and
glycoside-substituted silicones.

It is also possible for the preparations to contain more than one, particularly two different polymers with the same charge and/or in each case an ionic and an amphoteric and/or nonionic polymer. The other polymers (G) are present in the agents preferably in quantities of 0.05 to 10 wt. %, based on total weight of the agent. Quantities of 0.1 to 5, particularly 0.1 to 3 wt. %, are particularly preferred.

Silicones represent a particularly preferred group of ingredients.

Preferred agents according to the invention contain at least one silicone, preferably a silicone chosen from:
(i) polyalkyl siloxanes, polyaryl siloxanes, polyalkylaryl siloxanes, which are volatile or non-volatile, straight-chained, branched or cyclic, crosslinked or uncrosslinked;
(ii) polysiloxanes having one or more organofunctional groups in their general structure and chosen from:
a) substituted or unsubstituted aminated groups;
b) (per)fluorinated groups;
c) thiol groups;
d) carboxylate groups;
e) hydroxylated groups;
f) alkoxylated groups;
g) acyloxyalkyl groups;
h) amphoteric groups;
i) bisulfite groups;
j) hydroxyacylamino groups;
k) carboxy groups;
l) sulfonic acid groups; and
m) sulfate or thiosulfate groups;
(iii) linear polysiloxane (A)-polyoxyalkylene (B) block copolymers of the $(A-B)_n$ type with $n>3$;
(iv) grafted silicone polymers with an organic backbone that does not contain silicone, which consist of an organic main chain which is formed from organic monomers that do not contain silicone, on to which at least one polysiloxane macromer has been grafted in the chain and optionally on at least one end of the chain;
(v) grafted silicone polymers with a polysiloxane backbone on to which organic monomers that do not contain silicone have been grafted, which have a polysiloxane main chain on to which at least one polysiloxane macromer which does not contain any silicone has been grafted in the chain and optionally on at least one end of the chain;
or mixtures thereof.

Particularly preferred agents contain silicone(s) preferably in quantities of 0.1 to 10 wt. %, preferably from 0.25 to 7 wt. % and in particular from 0.5 to 5 wt. %, relative to the overall agent.

Particularly preferred agents according to the invention contain at least one silicone of the formula Si—I

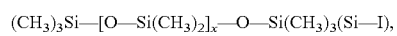

(Si—I), wherein x is a number from 0 to 100, preferably 0 to 50, more preferably 0 to 20 and particularly 0 to 10. These silicones are known under INCI nomenclature as DIMETHICONES.

Preferred silicones have viscosities at 20° C. of 0.2 to 2 mm$^2$s$^{-1}$, with silicones having viscosities of 0.5 to 1 mm$^2$s$^{-1}$ being particularly preferred.

Particularly preferred agents contain one or more amino functional silicones. Regardless of which amino functional silicone is used, preferred agents contain an amino functional silicone the amine value of which is 0.25 meq/g or higher, preferably 0.3 meq/g or higher, and particularly 0.4 meq/g or higher. Preferred agents contain, relative to their weight, 0.01 to 10 wt. %, preferably 0.1 to 8 wt. %, more preferably 0.25 to 7.5 wt. % and particularly 0.5 to 5 wt. % amino functional silicone(s).

Cyclic dimethicones known according to INCI as CYCLOMETHICONES can also be used. Here, preferred agents contain at least one silicone of formula Si—III

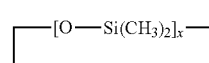

(Si-III)

wherein x is a number from 3 to 200, preferably 3 to 10, more preferably 30 to 7 and particularly 3, 4, 5 or 6.

For aesthetic reasons, "clear" products are often preferred by consumers. Preferred hair treatment agents are therefore transparent or translucent. Within the framework of the present invention, transparent or translucent refers to a composition having an NTU value of less than 100. The NTU value (Nephelometric Turbidity Unit, NTU) is a unit used in water treatment for turbidity measurements in fluids. It is the unit of turbidity of a fluid measured with a calibrated nephelometer.

Agents according to the invention have advantageous properties and also impart advantageous properties to hair treated therewith. Advantages have been observed particularly in hair and scalp treatment. For example, hair treatment agents according to the invention increase the elasticity of hairs treated therewith and lead to a strengthening of the internal structure of the hair fibers, which is reflected, for example, in higher melting points in differential thermal analysis.

An improvement in wet and dry combability is also demonstrated, together with a prevention of premature split ends in treated hair. On the skin and in particular the scalp, agents according to the invention cause an increase in elasticity and, surprisingly, sebum-regulating effects. The optical impression of "oily" skin or hair is thus avoided or diminished.

The present invention also provides for the use of agents according to the invention to improve at least one of the following properties:
- tensile strength of keratinous fibers, in particular human hairs;
- stabilizing the moisture balance of keratinous fibers, in particular human hairs;
- combability of keratinous fibers, in particular human hairs;
- delaying the ageing process of keratinous fibers, in particular human hairs;
- restructurability of keratinous fibers, in particular human hairs, during and after the perming process;
- reduction of the loss of elasticity of keratinous fibers, in particular human hairs, when damaged by atmospheric influences.

Statements relating to the agents according to the invention apply mutatis mutandis to other preferred embodiments of the use according to the invention.

The following examples are intended to explain the subject matter of the invention in more detail without restricting it.

EXAMPLES

| Shampoo | wt. % |
| --- | --- |
| Citric acid, anhydrous | 0.5 |
| Sodium lauryl ether sulfate.25% | 50.0 |
| Disodium cocoamphodiacetate | 7.0 |
| Salicylic acid | 0.2 |
| D-Panthenol 75% | 0.5 |
| Na benzoate | 0.5 |
| Euperlan PK 3000 AM | 2.0 |
| Cetiol HE | 1.0 |
| Oligopeptide mixture# | 0.01 |
| Polymer JR 400 | 0.5 |
| Perfume | 0.5 |
| PEG-40 Hydrogenated Castor Oil 455 | 1.0 |
| *Macadamia* nut oil, refined | 0.2 |
| Sodium chloride fine-medium | 0.5 |
| Water, deionized | To 100 | containing - relative to their weight - at least 10 wt. % of a mixture of oligopeptides comprising 8 amino acids with the amino acid sequence Tyr-Glu-Glu-Glu-Ile-Arg-Val-Leu and oligopeptides comprising 9 amino acids with the amino acid sequence Leu-Tyr-Glu-Glu-Glu-Ile-Arg-Val-Leu

| | |
| --- | --- |
| Euperlan ® PK3000 | approx. 60-64% solids; INCI name: glycol distearate, glycerol, laureth-4, cocamidopropyl betaine (Cognis) |
| Cetiol ® HE | cocomonoglyceride with approx. 7.3 EO units (INCI name: PEG-7 glyceryl cocoate) (Cognis) |
| Polymer JR ® 400 | quaternized hydroxyethyl cellulose (INCI name: polyquaternium-10) (Amerchol) |

| Regenerative cream | wt. % |
| --- | --- |
| Paraffinum Liquidum | 1 |
| Dehyquart F 75 | 2 |
| Oligopeptide mixture# | 0.1 |
| Varisoft W 75 PG | 1.5 |
| Cetearyl alcohol | 3.5 |
| Emulmetik 100 | 0.4 |
| Propylparaben | 0.15 |
| Cutina CP | 0.7 |
| Stearamidopropyldimethylamine | 1 |
| Dehyquart A CA | 3 |
| Citric acid | 0.5 |
| Methylparaben | 0.15 |
| Phenoxyethanol, pure | 0.4 |
| D-Panthenol 75% | 0.2 |
| Gluadin W 20 | 1 |
| Perfume | 0.4 |
| Salcare SC 96 | 1 |
| Water, deionized | To 100 | containing - relative to its weight - at least 10 wt. % of a mixture of oligopeptides comprising 8 amino acids with the amino acid sequence Tyr-Glu-Glu-Glu-Ile-Arg-Val-Leu and oligopeptides comprising 9 amino acids with the amino acid sequence Leu-Tyr-Glu-Glu-Glu-Ile-Arg-Val-Leu

| | |
| --- | --- |
| Dehyquart ® F75 | fatty alcohol - methyltriethanolammonium methyl sulfate - dialkyl ester mixture (INCI name: distearoylethyl hydroxyethylmonium methosulfate, cetearyl alcohol) (Henkel) |
| Varisoft ® W 575 PG | INCI name: quaternium-87 (Goldschmidt) |
| Emulmetik ® 100 | lecithin (Degussa) |
| Cutina ® CP | cetyl palmitate (Cognis) |
| Dehyquart ® A-CA | trimethylhexadecyl ammonium chloride (approx. 24-26% active substance; INCI name: aqua (water), cetrimonium chloride) (Cognis) |
| Gluadin ® W20 | wheat protein hydrolyzate (min. 20% solids; INCI name: aqua (water), hydrolyzed wheat protein, sodium benzoate, phenoxyethanol, methylparaben, propylparaben) (Cognis) |
| Salcare ® SC 96 | approx. 50% active substance content; INCI name: polyquaternium-37, propylene glycol dicaprylate/dicaprate, PPG-1 trideceth-6 (CIBA) |

| Leave-in Treatment | wt. % |
| --- | --- |
| Synthalen K | 0.25 |
| Sepigel 305 | 1.0 |
| Dehyquart F 75 | 0.5 |
| Polymer JR 400 | 0.3 |
| Neutrol TE | 0.4 |
| Oligopeptide mixture# | 0.1 |
| Perfume | 0.3 |
| D-Panthenol 75% | 0.5 |
| Luviskol K 30 powder | 0.5 |
| Gafquat 755N | 0.5 |
| Dow Corning 1401 Fluid | 1.0 |
| Ethanol 96% DEP denatured | 15.0 |
| Sepigel 305 | 1.6 |
| Water, deionized | To 100 | containing - relative to their weight - at least 10 wt. % of a mixture of oligopeptides comprising 8 amino acids with the amino acid sequence Tyr-Glu-Glu-Glu-Ile-Arg-Val-Leu and oligopeptides comprising 9 amino acids with the amino acid sequence Leu-Tyr-Glu-Glu-Glu-Ile-Arg-Val-Leu

| | |
| --- | --- |
| Synthalen ® K | polyacrylic acid (approx. 89% active substance content; INCI name: carbomer) (3V Sigma) |
| Neutrol ® TE | N,N,N',N'-tetrakis-(2-hydroxypropyl)ethylene-diamine (INCI name: tetrahydroxypropyl ethylenediamine) (BASF) |
| Luviskol ® K30 | polyvinylpyrrolidone (100% solids; INCI name: PVP) (BASF) |
| Gafquat ® 755 | dimethylaminoethyl methacrylate - vinylpyrrolidone copolymer, quaternized with diethyl sulfate (approx. 19% solids in water; INCI name: polyquaternium-11) (ISP) |
| Dow Corning 1401 ® | dimethyl cyclosiloxane dimethylpolysiloxanol mixture (approx. 13% solids; INCI name: cyclomethicone, dimethiconol) (Dow Corning) |

-continued

| | |
|---|---|
| Sepiger ® 305 | approx. 45-49% solids; INCI name: polyacrylamide, $C_{13-14}$ isoparaffin, laureth-7) (Seppic) |

| Intensive conditioner | wt. % |
|---|---|
| Varisoft W 75 PG | 1.5 |
| Paraffinum Liquidum | 1.0 |
| Dehyquart F 75 | 2.0 |
| Stearamidopropyl dimethylamine | 1.0 |
| Oligopeptide mixture[#] | 0.1 |
| Cetearyl alcohol | 5.0 |
| Cutina GMS-V | 1.0 |
| Citric acid | 0.3 |
| Dehyquart A CA | 5.0 |
| Salcare SC 96 | 0.5 |
| Perfume | 0.4 |
| D-Panthenol 75% | 0.5 |
| Water, deionized | To 100 |

[#]containing - relative to their weight - at least 10 wt. % of a mixture of oligopeptides comprising 8 amino acids with the amino acid sequence Tyr-Glu-Glu-Ile-Arg-Val-Leu and oligopeptides comprising 9 amino acids with the amino acid sequence Leu-Tyr-Glu-Glu-Glu-Ile-Arg-Val-Leu
Cutina ® GMS-V glycerol mono/dipalmitate/stearate (INCI name: glyceryl stearate) (Cognis)

Proof of Action

By determining the modulus of elasticity using tensile tests in Hooke's range, individual hairs were tested to find out to what extent an addition of 0.01% of an oligopeptide mixture which—relative to its weight—contains at least 10 wt. % of a mixture of oligopeptides comprising 8 amino acids with the amino acid sequence Tyr-Glu-Glu-Glu-Ile-Arg-Val-Leu and oligopeptides comprising 9 amino acids with the amino acid sequence Leu-Tyr-Glu-Glu-Glu-Ile-ArgVal-Leu (corresponding to a concentration of oligopeptides according to the invention used of at least 0.001 wt. %, relative to the shampoo) in a basic shampoo formulation has a positive effect on the elasticity of the hair structure after 50 automated treatment cycles also comprising, in addition to shampooing, rinsing and drying, exposure of the hair to simulated sunlight. Untreated hair was used as reference.

For the measurements, European natural hair, remis, color 7/0 from Kerling was used.

For the measurements, 40 individual hairs were each divided into three parts, cycle shifted and allocated into three test series—

1$^{st}$ test series basic shampoo
2$^{nd}$ test series basic shampoo+0.01% oligopeptide mixture
3rd reference, untreated hair Shampoo Formulation
Basic Shampoo:
 43.12%—sodium laureth sulfate 25%
 0.50%—citric acid monohydrate
 7.00%—disodium cocoamphodiacetate
 0.50%—Na benzoate
 0.20%—salicylic acid
 48.68%—water
Amount of reference solution or test solution applied 160 ml
Preheating of solution: 5 minutes at 38° C.
Exposure time of hair in above solutions 3 minutes at 38° C.
Rinse time of each solution 2 minutes.
30 minutes drying at 80° C.
60 minutes irradiation at 765 Watt, black panel temperature 50° C., sample chamber temperature 37 or 38° C.

Conducting the Measurements:

1. 50 automated treatment and exposure cycles (mfa) were carried out for test series 1 and 2.

2. Cross-sectional area of hair was determined for test series 1, 2 and 3.

3. By means of wet tensile measurements in Hooke's range, the modulus of elasticity of all the individual hairs was determined for test series 1, 2 and 3.

Test Results for The Elasticity Measurements

Test results for the elasticity measurements

| Cross-sectional area of hair [μm$^2$] | Elastic modulus [N/m$^2$] | Elastic gradient [N/μm$^2$/mm] | Elastic extension [%] |
|---|---|---|---|
| Test series no. 1: 50 passes with the mfa using basic shampoo ||||
| 3319.6 | 2.08E+09 | 6.81E−05 | 2.33E−00 |
| Test series no. 2: 50 passes with the mfa using basic shampoo + 0.01% oligopeptide mixture ||||
| 3242.6 | 2.18E+09 | 7.13E−05 | 2.27E−00 |
| Test series no. 3: Untreated hair ||||
| 3289.5 | 2.24E+09 | 7.38E−05 | 2.12E−05 |
| Comparison test series no. 1 v. no. 2: t-Test: two-sided for independent random samples ||||
| No difference | Significant difference | Significant difference | Significant difference |
| Comparison test series no. 1 v. no. 3: t-Test: two-sided for independent random samples ||||
| No difference | Significant difference | Significant difference | Significant difference |
| Comparison test series no. 2 v. no. 3: t-Test: two-sided for independent random samples ||||
| No difference | No difference | No difference | No difference |

Conclusion

Using the 50× treatment and irradiation cycles (mfa) and subsequent tensile tests, a significant positive effect of the oligopeptide mixture on the elasticity of the hair structure was found. The addition of 0.01% of the oligopeptide mixture (corresponding to a concentration of oligopeptides according to the invention used of at least 0.001 wt. %, relative to the shampoo) to a basic shampoo led to a significant increase in the modulus of elasticity of the hairs. As a result of this addition, the elasticity after 50 treatment and irradiation cycles (mfa) remains at the level of undamaged hairs.

We claim:

1. Hair treatment agent, comprising 0.00001 to 0.05 wt. % based on total weight of the agent, of at least one oligopeptide having at least one amino acid sequence Glu-Glu-Glu

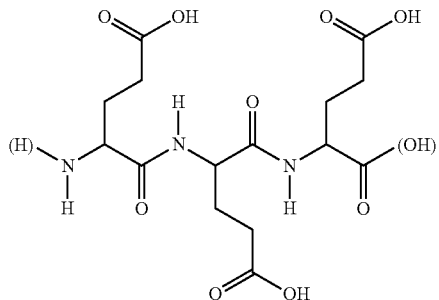

wherein the amino group is present in a free or protonated form and the carboxy groups are present in a free or deprotonated form, wherein the oligopeptide has at least one amino acid sequence Tyr-Glu-Glu-Glu-Ile-Arg-Val-Leu (SEQ ID NO: 7)

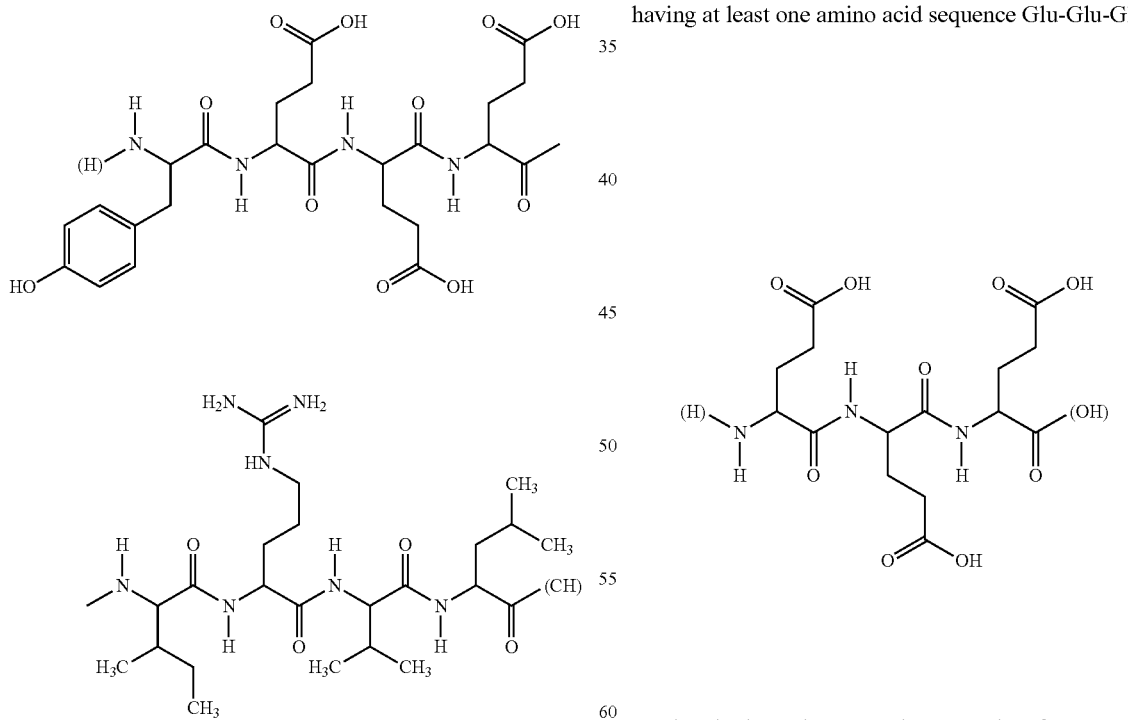

wherein the amino groups are present in a free or protonated form and the carboxy groups are present in a free or deprotonated form.

2. Hair treatment agent according to claim 1, wherein the oligopeptide comprises 5 to 15 amino acids.

3. Hair treatment agent according to claim 1, wherein the oligopeptide has a molar mass of 650 to 3000 Da.

4. Hair treatment agent according to claim 1, wherein at least 0.1 wt. % of all keratinous peptides present in the agent have the amino acid sequence Tyr-Glu-Glu-Glu-Ile-Arg-Val-Leu (SEQ ID NO: 7).

5. Hair treatment agent according claim 1 further comprising 0.5 to 70 wt.%, based on total weight of the agent, anionic and/or nonionic and/or cationic and/or amphoteric surfactant(s).

6. Hair treatment agent according to claim 1 further comprising 0.05 to 7.5 wt.%, based on total weight of the agent, of one or more cationic polymers.

7. Hair treatment agent according to claim 6, wherein the one or more cationic polymers are chosen from poly(methacryloyloxyethyl trimethylammonium chloride), polyquaternium-37, quaternized cellulose derivatives, polyquaternium 10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium 2, polyquaternium-7, polyquaternium 17, polyquaternium 18, polyquaternium 24, polyquaternium 27 or mixtures thereof.

8. Hair treatment agent, comprising 0.00001 to 0.05 wt. % based on total weight of the agent, of at least one oligopeptide having at least one amino acid sequence Glu-Glu-Glu wherein the amino group is present in a free or protonated form and the carboxy groups are present in a free or deprotonated form, and wherein the hair treatment agent further comprises at least two oligopeptides A and B which differ from one another, wherein oligopeptide A has the amino acid sequence Leu-Tyr-Glu-Glu-Glu-Ile-Arg-Val-Leu (SEQ ID NO: 8)

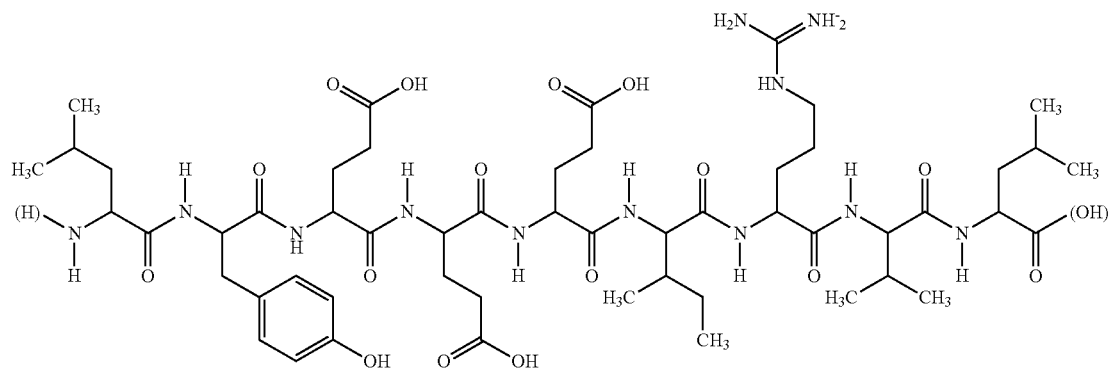
wherein the amino groups are present in a free or protonated form and the carboxy groups are present in a free or deprotonated form, and
oligopeptide B has the amino acid sequence Tyr-Glu-Glu-Glu-Ile-Arg-Val-Leu (SEQ ID NO: 7)
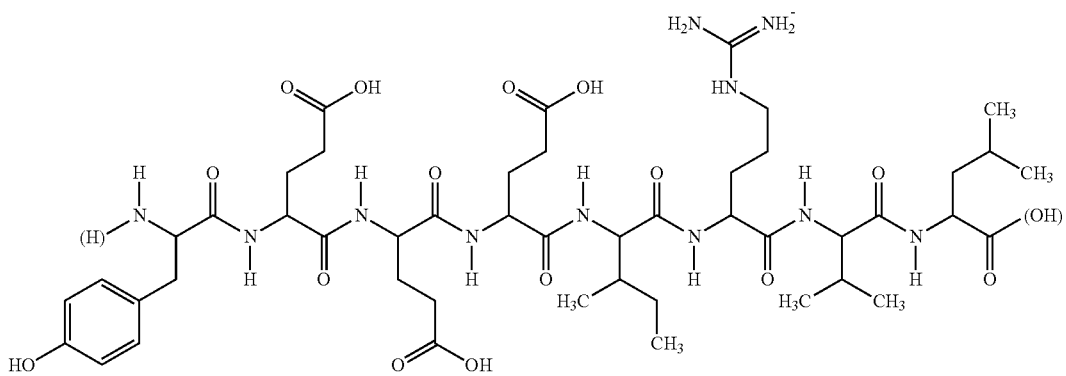
wherein the amino groups may be present in a free or protonated form and the carboxy groups may be present in a free or deprotonated form.
* * * * *

SEQUENCE LISTING

<160> NUMBER OF SEQ ID NOS: 11

<210> SEQ ID NO 1
<211> LENGTH: 3
<212> TYPE: PRT
<213> ORGANISM: Artificial
<220> FEATURE:
<223> OTHER INFORMATION: Synthetic Construct

<400> SEQUENCE: 1

Glu Glu Glu
1

<210> SEQ ID NO 2
<211> LENGTH: 4
<212> TYPE: PRT
<213> ORGANISM: Artificial
<220> FEATURE:
<223> OTHER INFORMATION: Synthetic Construct

<400> SEQUENCE: 2

Tyr Glu Glu Glu
1

<210> SEQ ID NO 3
<211> LENGTH: 4
<212> TYPE: PRT
<213> ORGANISM: Artificial
<220> FEATURE:
<223> OTHER INFORMATION: Synthetic Construct

<400> SEQUENCE: 3

Glu Glu Glu Ile
1

<210> SEQ ID NO 4
<211> LENGTH: 5
<212> TYPE: PRT
<213> ORGANISM: Artificial
<220> FEATURE:
<223> OTHER INFORMATION: Synthetic Construct

<400> SEQUENCE: 4

Tyr Glu Glu Glu Ile
1               5

<210> SEQ ID NO 5
<211> LENGTH: 6
<212> TYPE: PRT
<213> ORGANISM: Artificial
<220> FEATURE:
<223> OTHER INFORMATION: Synthetic Construct

<400> SEQUENCE: 5

Tyr Glu Glu Glu Ile Arg
1               5

<210> SEQ ID NO 6
<211> LENGTH: 7
<212> TYPE: PRT
<213> ORGANISM: Artificial
<220> FEATURE:
<223> OTHER INFORMATION: Synthetic Construct

<400> SEQUENCE: 6

Tyr Glu Glu Glu Ile Arg Val

```
1               5

<210> SEQ ID NO 7
<211> LENGTH: 8
<212> TYPE: PRT
<213> ORGANISM: Artificial
<220> FEATURE:
<223> OTHER INFORMATION: Synthetic Construct

<400> SEQUENCE: 7

Tyr Glu Glu Glu Ile Arg Val Leu
1               5

<210> SEQ ID NO 8
<211> LENGTH: 9
<212> TYPE: PRT
<213> ORGANISM: Artificial
<220> FEATURE:
<223> OTHER INFORMATION: Synthetic Construct

<400> SEQUENCE: 8

Leu Tyr Glu Glu Glu Ile Arg Val Leu
1               5

<210> SEQ ID NO 9
<211> LENGTH: 5
<212> TYPE: PRT
<213> ORGANISM: Artificial
<220> FEATURE:
<223> OTHER INFORMATION: Synthetic Construct

<400> SEQUENCE: 9

Glu Glu Glu Ile Arg
1               5

<210> SEQ ID NO 10
<211> LENGTH: 6
<212> TYPE: PRT
<213> ORGANISM: Artificial
<220> FEATURE:
<223> OTHER INFORMATION: Synthetic Construct

<400> SEQUENCE: 10

Glu Glu Glu Ile Arg Val
1               5

<210> SEQ ID NO 11
<211> LENGTH: 7
<212> TYPE: PRT
<213> ORGANISM: Artificial
<220> FEATURE:
<223> OTHER INFORMATION: Synthetic Construct

<400> SEQUENCE: 11

Glu Glu Glu Ile Arg Val Leu
1               5
```